United States Patent [19]
Fujimoto

[11] Patent Number: 5,339,821
[45] Date of Patent: Aug. 23, 1994

[54] HOME MEDICAL SYSTEM AND MEDICAL APPARATUS FOR USE THEREWITH

[75] Inventor: Jun Fujimoto, Tokyo, Japan

[73] Assignees: Seta Co., Ltd.; NASA Corporation Co., Ltd., both of Tokyo, Japan

[21] Appl. No.: 966,726

[22] Filed: Oct. 26, 1992

[30] Foreign Application Priority Data

Feb. 13, 1992 [JP] Japan .................. 4-059477

[51] Int. Cl.⁵ .............................................. A61N 5/04
[52] U.S. Cl. .................... 128/700; 128/903; 128/904
[58] Field of Search ............... 128/670, 671, 696, 700, 128/903, 904, 906, 908

[56]  References Cited
U.S. PATENT DOCUMENTS

| | | | |
|---|---|---|---|
| 3,566,365 | 2/1971 | Ranson et al. | 128/906 |
| 3,566,370 | 2/1971 | Worthington et al. | 128/904 |
| 3,920,005 | 11/1975 | Gombrich et al. | 128/904 |
| 4,449,536 | 5/1984 | Weaver | 128/696 |
| 4,566,461 | 1/1986 | Lubell et al. | 128/700 |
| 4,722,349 | 2/1988 | Baumberg | 128/904 |
| 4,782,511 | 11/1988 | Nemec et al. | 128/904 |
| 4,803,625 | 2/1989 | Fu et al. | 128/908 |
| 4,838,275 | 6/1989 | Lee | 128/904 |

FOREIGN PATENT DOCUMENTS

0286456 10/1988 European Pat. Off. ............ 128/904

*Primary Examiner*—William E. Kamm
*Attorney, Agent, or Firm*—Notaro & Michalos

[57] ABSTRACT

A home medical system allows any patient or healthy person to measure his or her daily condition at home and undergo a check or an inquiry diagnosis by a medical specialist or doctor. The home medical system includes equipment for measuring the electrocardiogram and other heart conditions of a user, a display for explaining the procedure and a display for displaying thereon a result of a measurement by the equipment. A communication link connects the user's equipment to a medical institution for interconnecting the medical institution to the user's system so that medical personal at the medical institution can also review the measured results obtained by the user.

9 Claims, 6 Drawing Sheets

HOME MEDICAL SYSTEM AND MEDICAL APPARATUS FOR USE THEREWITH

BACKGROUND OF THE INVENTION

1. Field of the Invention

This invention relates to a home medical system and a medical apparatus for use therewith which are suitably applied when a common user who may be a patient having some disease effects management of the condition of the disease or health care at home.

2. Description of the Prior Art

In recent years, various home monitors have been put on the market in accordance with an increase of the necessity for the management of the condition of a disease or home care at home. However, they have not widely spread as yet due to the complexity of operation and the problem of the reliability and economy of the apparatus.

However, the variations of the blood pressure, for example, of a hypertension patient within a day and among days are very important problems. Particularly, the danger is pointed out that an excessive pressure reduction while hypertensive drugs are taken will reduce blood flow to the brain and the heart of an old hypertensive patient or a hypertension patient having a case history of cerebral infarction to cause an ischemic heart failure. Some person may, when the blood pressure is measured in front of a doctor, be strained and this can cause a rise of the blood pressure (so-called white robe hypertension) so that it is difficult to accurately grasp the original condition of the patient. Accordingly, it is very important to a hypertensive patient to observe the variation of the blood pressure in an ordinary condition at home over a long period of time.

Further, while it is recommended that a patient who has had a heart failure and has received an internal pace maker, measure his or her own pulse as a daily check in order to find out a pacing failure or a sensing failure of the internal pace maker, it is very difficult to grasp how may patients actually carry out the procedure every day. Accordingly, it is particularly useful to a pace maker embedded patient who works lively without having a particular complication that, if the patient makes use of a home medical system according to the present invention, a doctor can check an electrocardiogram monitor while the patient need not intentionally visit the hospital.

Similarly, it is an earnest desire to patients of ischemic heart diseases, patients of a heart failure, antiarrhythmic patients, patients of respiratory insufficiency, patients to whom the CAPD (continuous ambulatory peritoneal dialysis) has been performed and so forth that a patient can check the daily condition of its disease every day at home and a doctor can check the blood pressure and the electrocardiogram monitor so that the patient may live at rest every day.

On the other hand, even to healthy people having no disease, it is considered useful to early detection and early inquiry diagnosis of diseases of circulatory organs which are forecast to increase in the future that they can effect their health care easily at a low expense in order to achieve prevention and early detection of a disease.

SUMMARY OF THE INVENTION

It Is an object of the present invention to provide a home medical system and a medical apparatus for use with the home medical system by which a patient having a various disease or a healthy person can measure the daily condition of the disease or the condition of health at home to undergo a check or an inquiry diagnosis by a medical specialist and which are easy to operate, high in reliability and low in expense.

The above and other objects, features and advantages of the present invention will become apparent from the following description and the appended claims, taken in conjunction with the accompanying drawings in which like parts or elements are denoted by like reference characters.

DETAILED DESCRIPTION OF THE PREFERRED EMBODIMENT

Figure 1:
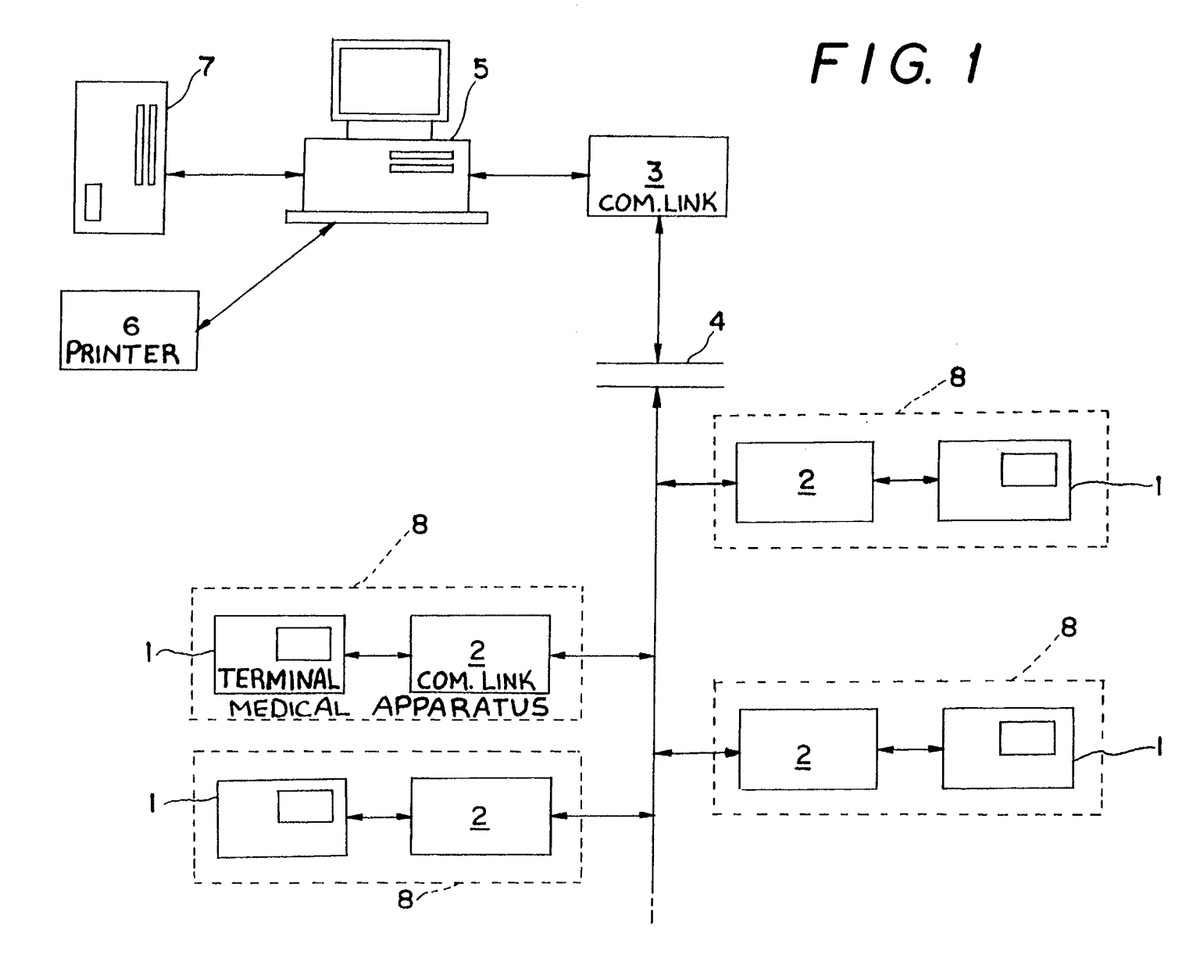
FIG. 1 is a block diagram showing an outline of a home medical system according to the present invention.

Referring first to FIG. 1, there is shown a home medical system according to a preferred embodiment of the present invention. The home medical system shown includes a medical terminal equipment 1 for measuring the blood pressure, the pulse, the electrocardiogram and so forth, and a user side communication apparatus or link 2. A medical apparatus 8 is constituted from the medical terminal equipment 1 and the user side communication apparatus 2 and is installed at home of each user. The home medical system further includes a medical institution side communication apparatus or link 3, and a telecommunication line 4 based on, for example, a CATV (cable television) system interconnects the communication apparatus 2 and 3. It is to be noted that, though not shown, the communication apparatus and 3 may naturally be interconnected alternatively by a telephone line or by way of a radio channel. The home medical system further includes a host computer 5 with a display unit on the medical institution side, and additional equipments such as a printer apparatus 6 and an external storage apparatus 7 are provided for the host computer 5.

Figure 2:
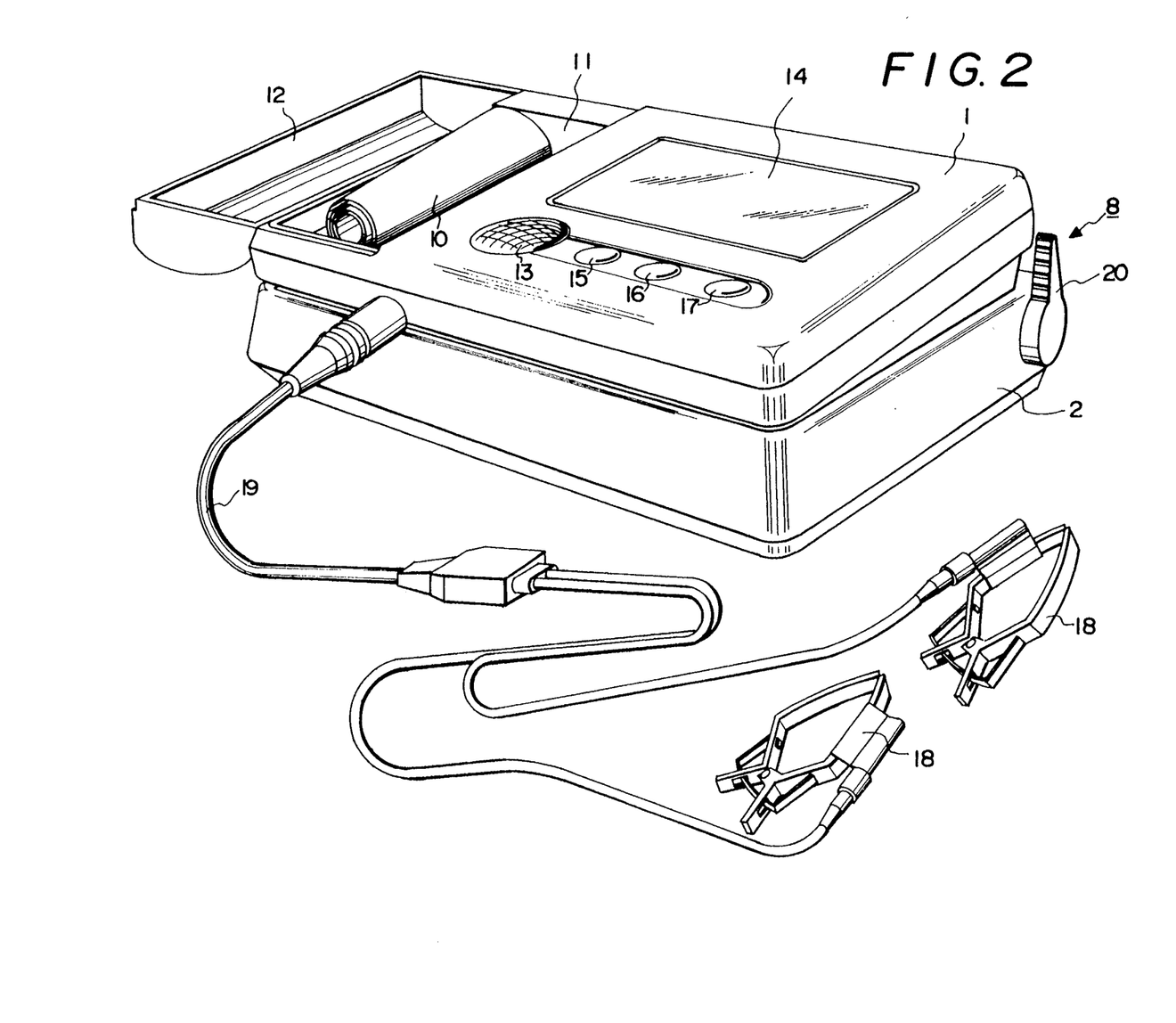
FIG. 2 is a perspective view of a medical terminal equipment for the user side to which the present invention is applied.

Referring now to FIG. 2, the medical apparatus 8 is shown in perspective view. The medical apparatus 8 shown includes the user side communication apparatus 2 and the medical terminal equipment 1 set in position on an upper face of the user side communication apparatus 2. An arm band 10 is accommodated in position at a side portion of an upper face of the medical terminal equipment 1. The arm band 10 is covered with a cover 12 which is hinged at a side portion thereof on one side of the medical terminal equipment 1. The medical terminal equipment 1 of the medical apparatus 8 includes a loudspeaker 13, a liquid crystal display apparatus 14 serving as display means, an operation button 15 for entering the reply of "Yes", another operation button 16 for entering the reply of "No", and a further operation button 17 for entering a selection. A pair of measuring electrodes 18 for measuring an electrocardiogram are removaly connected to a front portion of the medical terminal equipment 1 by way of a cable 19.

Figure 3:
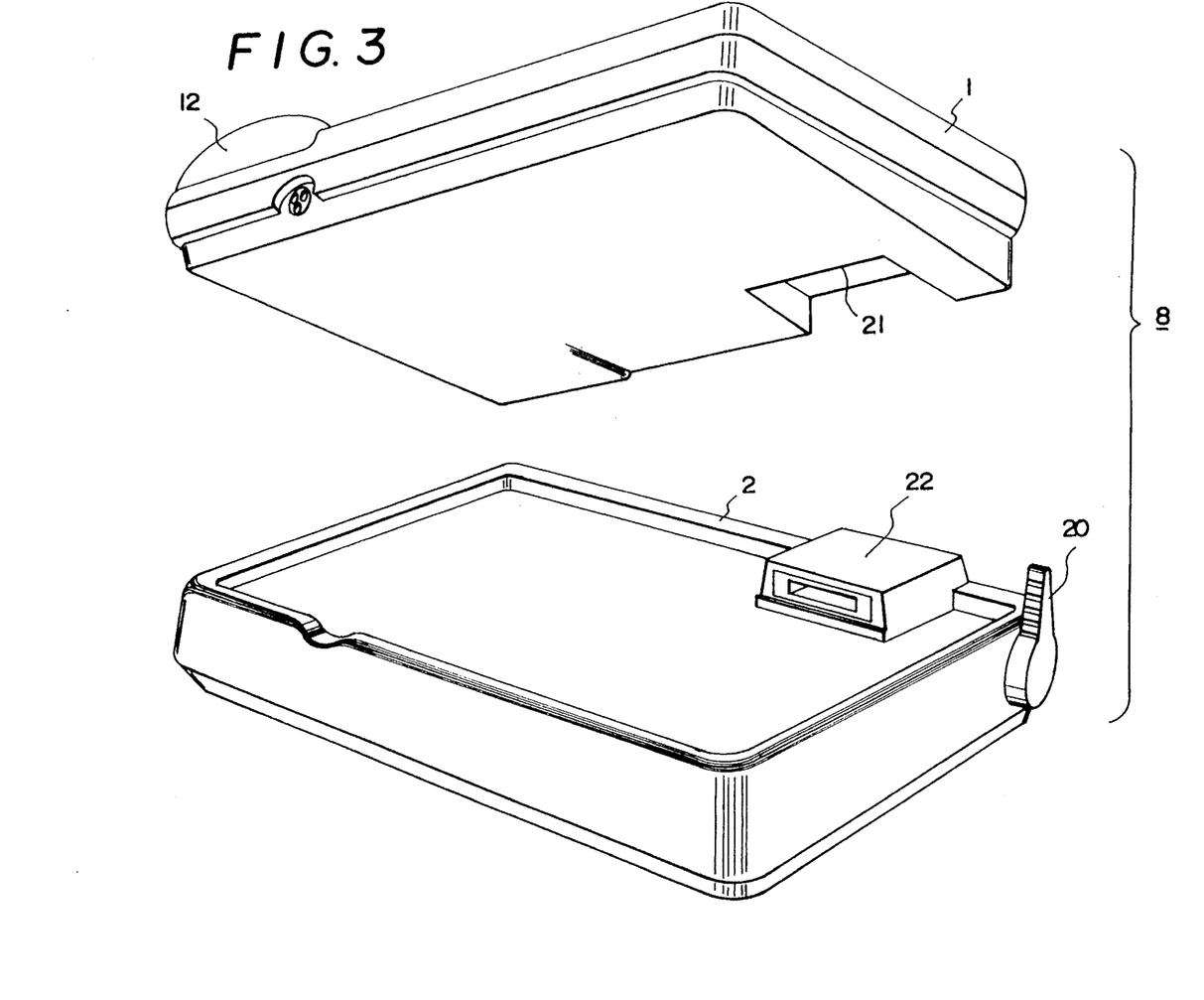
FIG. 3 is a fragmentary perspective view of the medical terminal equipment shown in FIG. 2.

Referring now to FIG. 3, the medical terminal equipment 1 is removably mounted on the user side communication apparatus 2, and if an operation lever 20 mounted on the user side communication apparatus 2 is tilted down and the medical terminal equipment 1 is pulled forwardly, then a connecting terminal 21 is removed from a connector 22 so that the medical terminal equipment 1 can thereafter be carried freely. It is to be noted that, in order to connect the thus removed medical terminal equipment 1 to the user side communication apparatus 2, the connecting terminal 21 is put to the connector 22 while the operation lever 20 is in the tilted down condition, and then the operation lever 20 is tilted up, thereby completing the connection of the medical terminal equipment 1 to the user side communication apparatus 2. Naturally, the present invention is not limited to the present embodiment with regard to the construction described just above. A battery power source is provided in the medical terminal equipment 1 as hereinafter described so that a measurement of the blood pressure and so forth and inputting of other data and so forth can be performed at a location remote from the user side communication apparatus 2.

Figure 4:
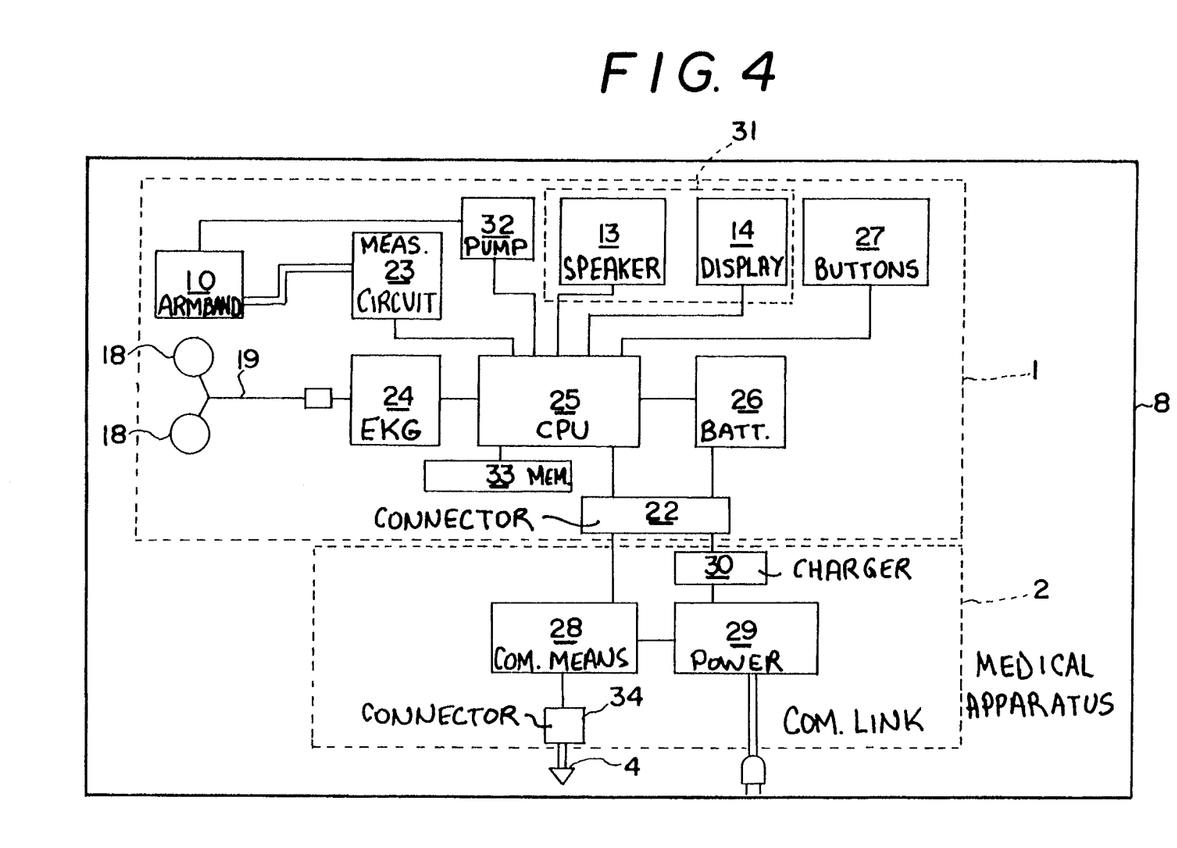
FIG. 4 is a block diagram of the medical terminal equipment shown in FIG. 2.

FIG. 4 shows in block diagram construction of the medical apparatus 8 which is constituted from the medical terminal equipment 1 and the user side communication apparatus 2. Referring to FIG. 4, the medical apparatus 8 includes the telecommunication line 4, the arm band 10, the loudspeaker 13 and the liquid display unit 14 of the STU type with a backlight. The medical apparatus 8 further includes a blood and pulse measuring circuit 23, an electrocardiogram measuring apparatus 24, a CPU (central processing unit) 25, a pump 32 and a memory 33. The memory 33 is backed up by a battery for exclusive use which is different from a battery which is hereinafter described. It is to be noted that the loudspeaker 13 and the liquid crystal display apparatus 14 are controlled by the CPU 23 and also constitute explaining means 31. The medical apparatus 8 includes a battery 26 and a plurality of operation buttons 27 which includes the operation buttons 15, 16 and 17 described above. The elements described above are included in the medical terminal equipment 1. Meanwhile, on the user side communication equipment 2 side, the medical apparatus 8 includes communicating means 28, a power source circuit 29, a battery charging circuit 30 and a connector 34. It is to be noted that, as described above, the telecommunication line 4 may be not a line of a cable television system but a telephone line or a telecommunication line including a radio antenna or the like.

Subsequently, an outline of the home medical system according to the present invention is described. First, since the battery 26 is built in the medical terminal equipment 1, the medical terminal equipment 1 can be used in a separate condition from the user side communication apparatus 2, and besides, it can be utilized by a plurality of users.

Figure 5:
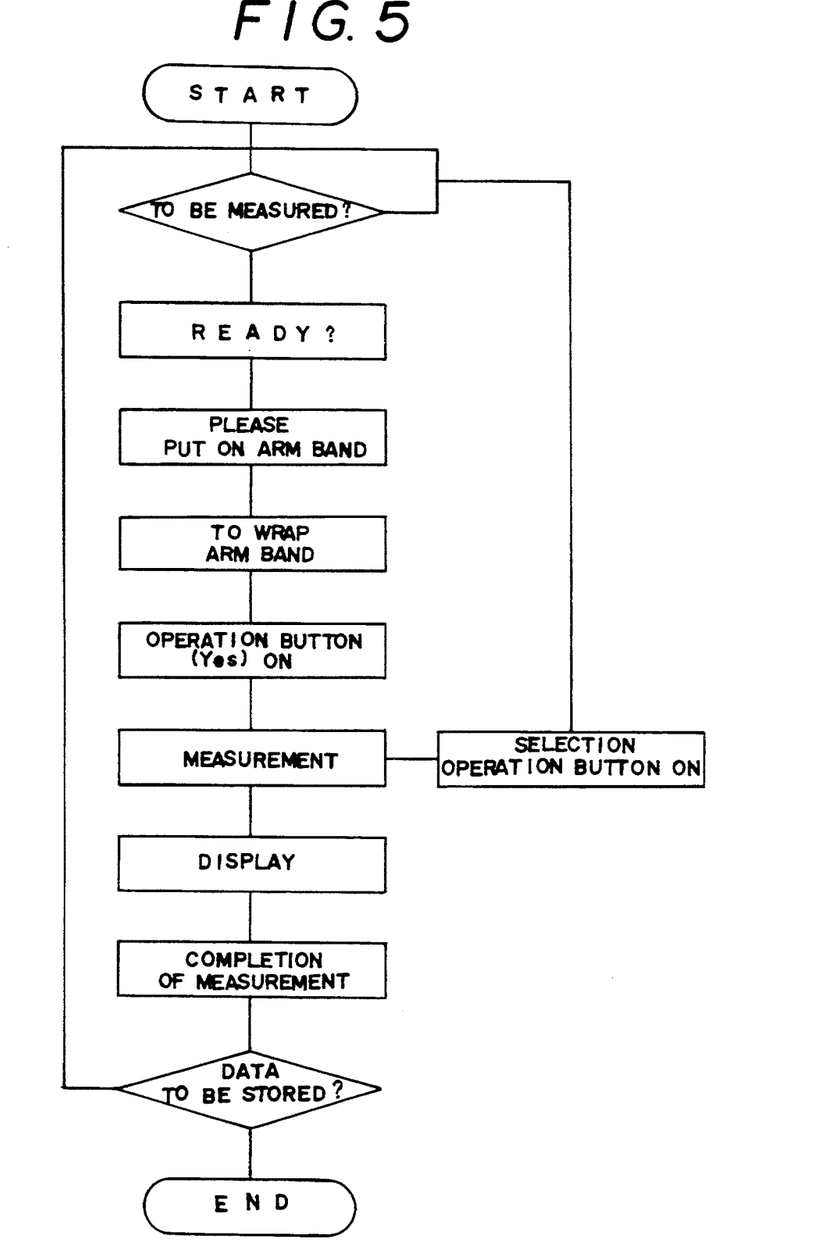
FIG. 5 is a flow chart illustrating a procedure of operation of the medical apparatus according to the present invention.
Figure 6:
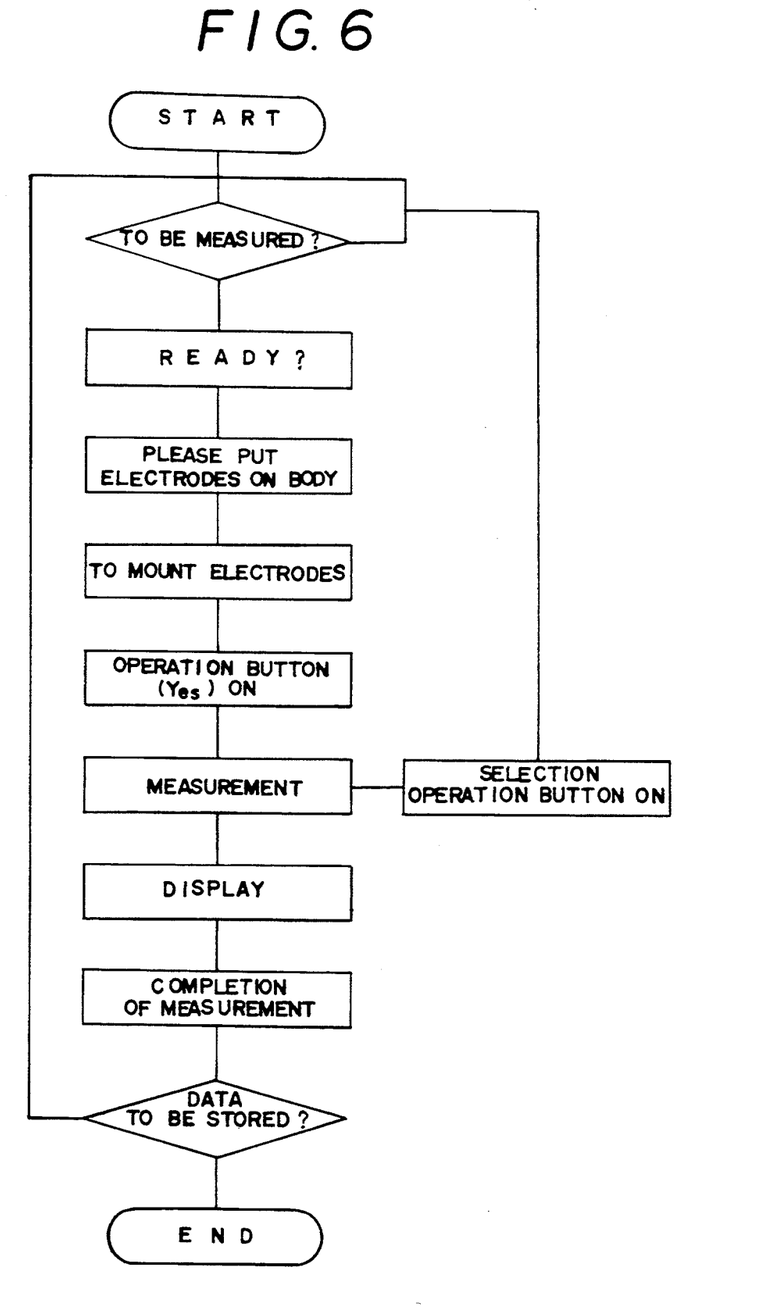
FIG. 6 is a flow chart illustrating another procedure of operation of the medical apparatus according to the present invention.

If a user depresses any one of the operation buttons 15, 16 and 17 (or alternatively a power source switch provided separately), the liquid crystal display unit 14 serving as display means is lit so that the date, the time, the registered number and so forth are displayed on the liquid crystal display unit 14. It is to be noted that, when no operation follows, the display by the liquid crystal display unit 14 is extinguished after 5 minutes or so in order to save the power of the battery power source, whereafter the liquid crystal display unit 14 enters into a waiting condition. Measurement, storage and so forth of various medical data after lighting of the liquid crystal display unit 14 are performed In such a manner, for example, as illustrated in FIGS. 5 and 6. Description of this is given below.

Measurement of the Blood Pressure and the Pulse (1) The medical terminal equipment 1 gives to the user a question "do you want to measure the blood pressure and the pulse" by way of the screen display of the liquid crystal display apparatus 14 and sound of the loudspeaker 13. The user enters its reply by means of either one of the operation buttons 15 and 16 for "Yes" and "No". In the case of the reply of "No", the control sequence returns to the start of the procedure without performing a measurement. On the contrary, in the case of the reply of "Yes", the control sequence advances to the next step.

(2) The medical terminal equipment 1 gives another question "are you ready ?" by way of the screen display and sound as described above.

(3) Subsequently, the medical terminal equipment 1 provides an instruction "please put on the arm band" to the user by way of the screen display and sound.

(4) The user will open the cover 12, pick up the arm band 10 provided on the medical terminal equipment 1 and wrap it around one of the arms.

(5) After the preparation for measurement is completed, the user will depress the operation button 15 for "Yes".

(6) In response to the depression of the operation button 15, air is automatically fed into the arm band 10 from the pump 32 and then discharged so that a measurement of the blood pressure and the pulse is started, for example, in accordance with the oscillometric method. Here, when the user wants to interrupt the measurement, the operation button 17 for "selection" will be depressed. Then, the measurement is interrupted immediately and the operation sequence returns to the step (1) described above.

(7) The result of the measurement is displayed in the following manner on the screen of the liquid crystal display unit 14.

```
Result of Measurement
Maximum Blood Pressure = 123 mmHg
Minimum Blood Pressure = 89 mmHg
Pulse = 60/minute
```

(8) The measurement of the blood pressure and the pulse is completed with this.

(9) Subsequently, the medical terminal equipment 1 gives a question "do you want to store the data ?" by way of the screen display and sound. If the operation button 16 for "No" is depressed, then the control sequence returns to the step (1) above without storing the measurement data. On the contrary, if the operation button 15 for "Yes" is depressed, then the measurement data are stored into the memory 33, thereby completing the procedure.

It is to be noted that, in the measurement of the blood pressure described above, the measurement is started with the maximum pressure value of 160 mmHg, but, if it is detected that the blood pressure exceeds the range, this is announced by sound and the measurement is started with the maximum pressure value of 240 mmHg. Further, while the arm band 10 is gradually pressurized upon measurement of the blood pressure and the pulse, in order to prepare for the case wherein a pressure higher than a necessary level is applied due to the failure of the pump 32 or the like, the medical apparatus 8 has, though not shown, a hardware safety circuit as well as a software safety circuit.

Subsequently, a measurement of an electrocardiogram is effected in accordance with such a procedure as illustrated in FIG. 6.

(1) The medical terminal equipment 1 gives a question "do you want to measure an electrocardiogram ?" to the user by way of the screen display of the liquid crystal display unit 14 and sound of the loudspeaker 13. The announcement by sound is repeated at an interval of time of 5 seconds until the user enters its reply of "Yes" by means of the operation button 15. The user will enter the reply by depression of either one of the operation buttons 15 and 16 for "Yes" and "No". In the case of the reply of "No", the control sequence returns to the start of the program. On the contrary, in the case of the reply of "Yes", the control sequence advances to the next step.

(2) The medical terminal equipment 1 gives a question "are you ready ?" by way of the screen display and sound.

(3) Subsequently, the medical terminal equipment 1 gives an instruction "put the electrodes on;" to the user by way of the screen display and sound.

(4) The user will put the measuring electrodes 18, which extend from the medical terminal equipment 1, on the arms of itself.

(5) After the user is prepared for measurement, the operation button 15 for "Yes" will be depressed.

(6) A measurement of an electrocardiogram is started. When the user wants to interrupt the measurement, the operation button 17 for "selection" will be depressed. As a result, the measurement is stopped immediately, and the control sequence returns to the step (1) above.

(7) An electrocardiographic waveform of the user during the measurement is displayed on the real time basis on the screen of the liquid crystal display unit 14.

(8) The medical terminal equipment 1 automatically ends Its measurement after one minute after completion of automatic gain adjustment after starting of the measurement.

(9) The medical terminal equipment 1 gives a question "do you want to store the data ?" by way of the screen display and sound. If the operation button 16 for "No" is depressed, then the control sequence returns to the first step (1) without storing the measurement data into the memory 33. On the contrary, if the operation button 15 for "No" is depressed, then the measurement data is stored into memory 33, thereby completing the procedure.

Subsequently, diagnosis inquiry using the system according to the present invention is described.

Minimum necessary questions for diagnosis inquiry are stored in advance in the host computer 5 and the medical terminal equipment 1, and consecutive numbers are applied in advance to the questions for diagnosis inquiry. On the medical institution side, a doctor will input the consecutive number or numbers of a question or questions for diagnosis inquiry to be asked to the user to the host computer 5, and the thus inputted number or numbers are stored into the host computer 5. After the inputting is completed, the host computer 5 transmits the inputted consecutive number or numbers of the questions for diagnosis inquiry to the medical apparatus 8 on the user side by way of the medical institution side communication apparatus 3. The medical apparatus 8 thus effects diagnosis inquiry of the received diagnosis inquiry question number or numbers to the user and transmits the result of the inquiry back to the host computer 5 by way of the user side communication apparatus 2. Since the diagnosis inquiry question number or numbers received by the medical apparatus 8 are stored in the memory 33 of the medical apparatus 8, the transmission from the host computer 5 must be performed only once. When it is desired to change the questions for diagnosis inquiry to the user, only the diagnosis inquiry question number or numbers stored in the host computer 5 should be changed. The host computer 5 transmits the thus changed diagnosis inquiry question number or numbers to the medical apparatus 8 of the user side by way of the medical institution side communication apparatus 3. Since the questions for diagnosis inquiry can be designated for each user, diagnosis inquiry effective for the disease or the condition of a particular user can be performed. The operation is performed in the following manner.

(1) The medical terminal equipment 1 gives a question "do you want to start diagnosis inquiry ?" by way of the screen display or sound.

(2) The user will enter its reply by depression of either one of the operation buttons 15 and 16 for "Yes" and In the case of the reply of "No", no diagnosis inquiry is effected. On the contrary, in the case of the reply of "Yes", diagnosis inquiry is started.

(3) The diagnosis inquiry proceeds in such a form that the user gives a reply by manual operation of either one of the operation buttons 15 and 16 for "Yes" and "No" to the question displayed on the screen of the liquid crystal display unit 14 like, for example, "Do you have a pain in the chest ?", "Yes" or "No" or "Do you feel languid ?", "Yes" or "No". When the user wants to interrupt the diagnosis inquiry, the operation button 17 for "selection" will be depressed. As a result, the diagnosis inquiry is interrupted and the procedure returns to the step (1) above.

(4) When all of the questions for diagnosis inquiry are completed, the medical terminal equipment 1 gives a question "do you wand to store the data ?" by way of the screen display and sound. If the operation button 16 for "No" is depressed, then the control sequence returns to the step (1) without storing the diagnosis inquiry data. On the contrary, if the operation button 15 for "Yes" is depressed, then the diagnosis inquiry data are stored into the memory 33, thereby completing the procedure.

Subsequently, inputting of data of the body temperature proceeds in the following manner.

(1) The medical terminal equipment 1 gives a question "do you want to record the body temperature ?" by way of the screen display of the liquid crystal display unit 14 and sound of the loudspeaker 13.

(2) The user will reply to the question by operation of the operation button 15 or 16 for "Yes" or "No". When the reply is "No", the body temperature is not recorded.

On the contrary, when the reply is "Yes", recording of the body temperature is started.

(3) The user will measure the body temperature by means of a clinical thermometer prepared by the user. Or else, the body temperature may have been measured in advance.

(4) Body temperature values from 35 to 45 degrees are displayed on the display screen, and also a cursor is displayed on the display screen. Depression of the operation button 15 or 16 for "Yes" or "No" moves the cursor in a direction in which the temperature value indicated by the cursor increases or decreases. The user will thus adjust the cursor to a body temperature value detected by the measurement by itself and depress the operation button 17 for "selection".

(5) The medical terminal equipment 1 gives a question "do you want to store the data ?" by way of the screen display and sound. If the operation button 16 for "No" is depressed, the control sequence returns to the step (1) without storing the body temperature data. On the contrary, if the operation button 15 for "Yes", then the body temperature data is stored into the memory 33, thereby completing the body temperature data inputting procedure.

An inputting procedure for data of the weight proceeds in the following manner.

(1) The medical terminal equipment 1 gives a question "do you want to record the weight ?" to the user by way of the screen display and sound.

(2) The user will reply to the question by operation of the operation button 15 or 16 for "Yes" or "No". When the reply is "No", the weight is not recorded. On the contrary, when the reply is "Yes", recording of the weight is started.

(3) The user will measure the weight by means of a weighing machine prepared by the user. Or else, the weight may have been measured in advance.

(4) The weight value of 50 Kg is displayed on the display screen of the liquid crystal display unit 14. Each depression of the operation button 15 or 16 for "Yes" or "No" increases or decreases the displayed weight value by 1 Kg. The user will thus adjust the displayed weight value to a weight value detected by the measurement by itself and depress the operation button 17 for "selection".

(5) The medical terminal equipment 1 gives a question "do you want to store the data ?" by way of the screen display and sound. If the operation button 16 for "No" is depressed, the control sequence returns to the step (1) without storing the weight value. On the contrary, if the operation button 15 for "Yes" is depressed, then the weight value is stored into the memory 33, thereby completing the weight data inputting procedure.

The medical apparatus 8 according to the present invention allows storage of data of a plurality of users into the memory 33 and also has a function of outputting, by accessing to it from the medical institution side, the stored data from the memory 33 making use of a CATV line, a telephone line or the like. When the medical apparatus 8 is to be used commonly by a plurality of users, identification information of entry numbers of the users must be inputted in advance. The inputting operation may involve displaying the identification information on the liquid crystal display unit 14 of the display means and depression of the operation button or buttons 15 or/and 16 for "Yes" and "No". The transmission of the data may be performed by accessing of the user side to the medical institution side or may be performed by accessing of the medical institution side so that the medical institution receives data stored in the user side communication apparatus 2. The number of times of measurement and inputting of various data within a day can be selected arbitrarily in accordance with an instruction of the medical institution.

Data transmitted from the user side communication apparatus 7 are set to the medical institution side communication apparatus 3 by means of a telephone line, a CATV line or a radio channel and stored into a hard disk or an opto-magnetic disk of the host computer 5 on the medical institution side. Then, the data are displayed immediately in accordance with the necessity. The host computer 5 on the medical institution side can naturally collect and store data for several hundreds to several thousands people using the external storage apparatus 7, automatically diagnose the collected data and transmit the result of the diagnosis to the user side, and pick up those data for which a diagnosis of a doctor is considered necessary and urge a diagnosis of a doctor. In addition, the host computer 5 can print the result of the diagnosis of the doctor together with data for the last one month by means of the printer 6 so that the data thus printed out may be delivered to the user. The automatic diagnosis of the host computer 5 involves, for example, checking of the pattern of the electrocardiographic waveform for the last one month to judge whether or not it has a significant variation or some abnormality, and if some abnormal condition is detected, a warning is issued. Further, the host computer 5 can provide a display of a variation graph of the blood pressure, the pulse, the body temperature, the weight and so forth for the last one month, compare the data with national average values of the sex and the age and give a notice of the result of the automatic diagnosis like, for example, "You are overweight: how about getting thin ?" or "Your blood pressure is excessively high: take care so as not to take too much salt.

It is to be noted that, while the communication apparatus may have a different construction depending upon communicating means, since the medical terminal equipment 1 automatically discriminates the construction and performs communications, for example, suitable for a CATV line, a telephone line or the like, only the communication apparatus may be replaced. Furthermore, data compression is performed for data to be communicated so that the time for which the line is used may be minimized. For example, if data of an electrocardiogram for one minute (about 15,000 bytes) are transmitted as they are at the baud rate of 2,400 BPS, then about 50 seconds are required, but if the data are compressed to 3,000 to 1,500 bytes or so and then transmitted, then the transmission is completed in about 5 to 10 seconds or so. Since the data compression has been developed originally, even if thus compressed data are stolen, it is difficult to decompress the compressed data and the secrecy is maintained. Further, since data for which the data compression has not been performed are enciphered, there is no possibility that the secret of an individual may leak to the outside.

Further, since the medical terminal equipment 1 is constructed so that it can store and execute a program transmitted to it from the host computer 5, it can perform expansion of or modification to the functions thereof. Further, since such program data are stored in the memory 33, the transmission from the host computer 5 is necessitated only once. Instructions and/or questions for diagnosis inquiry from the host computer 5 are stored into the memory 33 and displayed on the display unit 14 or announced repetitively from the loudspeaker 13.

Having now fully described the invention, it will be apparent to one of ordinary skill in the art that many changes and modifications can be made thereto without departing from the spirit and scope of the invention as set forth herein.

What is claimed is:

1. A medical system for measuring a user's blood pressure, pulse and electrocardiogram at home, and for communication between the user and a medical institution; the system comprising:

a home medical terminal for use by the user, the terminal including an arm band for measuring the user's blood pressure and pulse; a pair of measuring electrodes for measuring the user's electrocardiogram; explaining means for questioning a user with on-line and with preselected questions, and for presenting and explaining a measurement procedure to the user for use by the user to take measurements using said arm band and said measuring electrodes; a plurality of operation buttons operable by the user and operatively connected to the explaining means for inputting responses to the questions and for interacting with the explaining means to proceed through a measurement procedure; the home medical terminal also including display means for displaying a measurement by said arm band and a measurement by said electrodes, said display means also being operatively connected to said explaining means for displaying the questions and for presenting and explaining the measurement procedures; the home medical terminal further included a memory for storing the results of the measurements, and the answers to the questions; and a home central processing unit operatively connected to said display means, to said operation buttons, to said arm band, to said electrodes, to said explaining means and to said memory, for operating said arm band and electrodes to make the measurements, to operate said explaining means to question the user and present and explain measurement procedures to the user, and to receive signals from the operation buttons and to drive the display means and memory;

home communication means operatively connected to said home central processing unit for transmitting and receiving signals including the on-line questions for the user, responses to and from the user to those questions, and the measurements taken by the user;

institute communication means;

a communication line operatively connected between the home communication means and the institute communication means for transmitting and receiving signals therebetween;

a host computer operatively connected to the institution communication means and at the medical institution;

question means operatively connected to the host computer for initiating on-line and preselected questions for diagnosis inquiry to the host computer which are transmitted between the home and institution communication means over the communication line to the explaining means for providing questioning of the user; and attachment means operatively connected to the host computer for storing and displaying information from the host computer, received through the home and institution communication means over the communication line, and including the results of the measurements taken by the user and stored in the memory.

2. A medical system according to claim 1, wherein said communication line comprises a CATV line.

3. A medical system according to claim 1, wherein said communication line comprises a radio channel.

4. A medical system according to claim 1, including input means operably connected to said home central processing unit for use by the user to input body temperature and a weight of the user as part of the answer to the questions posed to the user by the explaining means.

5. A medical system according to claim 1, wherein said explaining means includes a display unit and a loudspeaker.

6. A medical system according to claim 1, wherein said communication line is a telephone line.

7. A medical apparatus, comprising:

a medical terminal equipment for a patient; and patient side communication means;

said medical terminal equipment including an arm band for measuring a blood pressure and a pulse of the patient, a pair of measuring electrodes for measuring an electrocardiogram of the patient, explaining means for explaining a procedure and a method of a measurement by said arm band and said measuring electrodes and for displaying on-line and preselected questions to the user, operation buttons for imputing a result of the measurement and answering to a question from a medical institution, display means for displaying thereon a result of the measurement by said measuring electrodes, for displaying the data, and for displaying the questions for diagnosis inquiry from the medical institution, a memory for storing therein the result of the measurement by said arm band and said measuring electrodes, the data, the questions for diagnosis inquiry, and answers to the questions, and a central processing unit for controlling said medical terminal apparatus; and said patient communication means including a power source circuit and a communication unit for transmitting and receiving the result of the measurement, the data, the question for diagnosis inquiry and the answers to the questions, as well as on-line questions from the medical institution, the patient communication means also operating to transmit to the medical institution a mixture of answers to the on-line and preselected questions.

8. A medical apparatus according to claim 7, wherein said medical terminal equipment and said patient side communication means are removably coupled to each other, and said medical terminal equipment further includes a built-in battery.

9. A medical apparatus according to claim 7, wherein said user side communication means includes data compressing means for compressing data to be transmitted.

* * * * *